(12) United States Patent
Kim et al.

(10) Patent No.: US 8,668,884 B2
(45) Date of Patent: Mar. 11, 2014

(54) GENERATING APPARATUS, REPRODUCING APPARATUS AND REPRODUCING METHOD OF CONTENTS WITH SMELL REPRODUCING INFORMATION

(75) Inventors: Myungeun Kim, Daejeon (KR); Hyoungsun Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 746 days.

(21) Appl. No.: 12/581,520

(22) Filed: Oct. 19, 2009

(65) Prior Publication Data
US 2010/0114819 A1    May 6, 2010

(30) Foreign Application Priority Data
Oct. 31, 2008    (KR) .................. 10-2008-0107754

(51) Int. Cl.
*A61L 9/00* (2006.01)
*A24F 25/00* (2006.01)
*G06F 15/16* (2006.01)
*F24F 7/00* (2006.01)
*G03B 21/32* (2006.01)
*B67D 5/62* (2006.01)
*G06F 17/00* (2006.01)

(52) U.S. Cl.
USPC ............... 422/306; 239/53; 239/66; 709/200; 707/3; 707/616; 236/49.3; 352/85; 222/146.5; 700/239; 700/241

(58) Field of Classification Search
USPC ........ 239/34, 53, 66, 74, 81, 86, 91; 422/1, 5, 422/105, 119, 123, 306, 900; 709/200; 707/3, 616; 236/49.3; 352/85; 222/146.5; 700/239, 241
See application file for complete search history.

(56) References Cited

U.S. PATENT DOCUMENTS

2005/0278224 A1* 12/2005 Bannai et al. .................. 705/22

FOREIGN PATENT DOCUMENTS

| KR | 1996-0004813 | 5/1994 |
| KR | 10-2006-0054976 | 5/2006 |

OTHER PUBLICATIONS

Korean Office Action issued Apr. 23, 2010 in corresponding Korean Application No. 10-2008-0107754.

* cited by examiner

*Primary Examiner* — Monzer R Chorbaji
(74) *Attorney, Agent, or Firm* — Staas & Halsey LLP

(57) ABSTRACT

The present invention provides the identification codes to the plurality of smell information and databases them, making it possible to identify the information on each smell and adds the smell data and smell reproducing information for at least one smell to the media data, making it possible to provide the contents with the plurality of smell reproducing information. Further, the smell diffusing apparatus includes the plurality of smell diffusing components to combine at least two smell diffusing components corresponding to the smell data and discharge them to the outside such that it can reproduce complex smells, thereby making it possible to effectively process a plurality of smell information.

4 Claims, 7 Drawing Sheets

(a)

| REPRODUCING TIME POINT | KIND OF SMELL | CONCENTRATION | SMELL DIFFUSING INTERVAL | SMELL DIFFUSING DIRECTION |
|---|---|---|---|---|
| $T_1 : T_2$ | A | 5 | 3 | 5° |
| $T_3 : T_4$ | B | 5 | 4 | 0° |
| $T_4 : T_5$ | B | 5 | 4 | 0° |
|  | C | 7 | 4 | 0° |
| $T_5 : T_6$ | C | 7 | 4 | 0° |
| $T_7 : T_8$ | D | 4 | 2 | 3° |
|  | E | 4 | 2 | 3° |

(b)

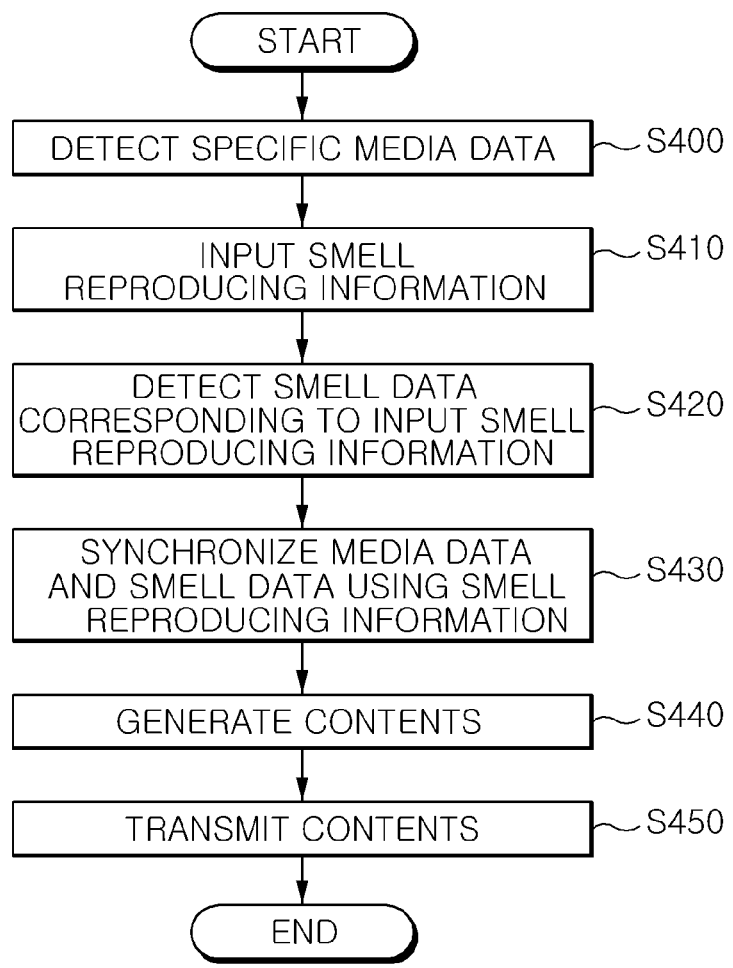

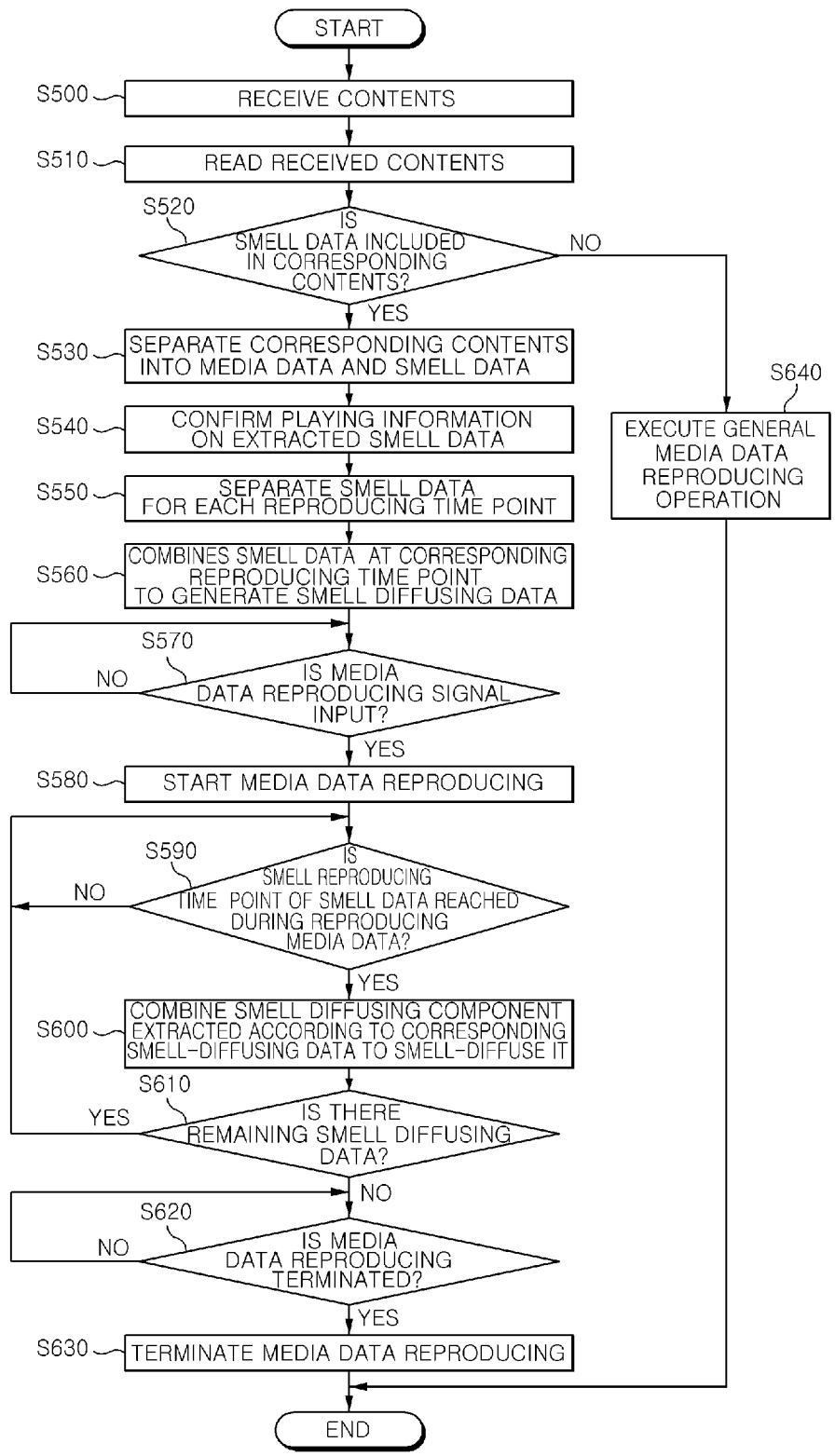

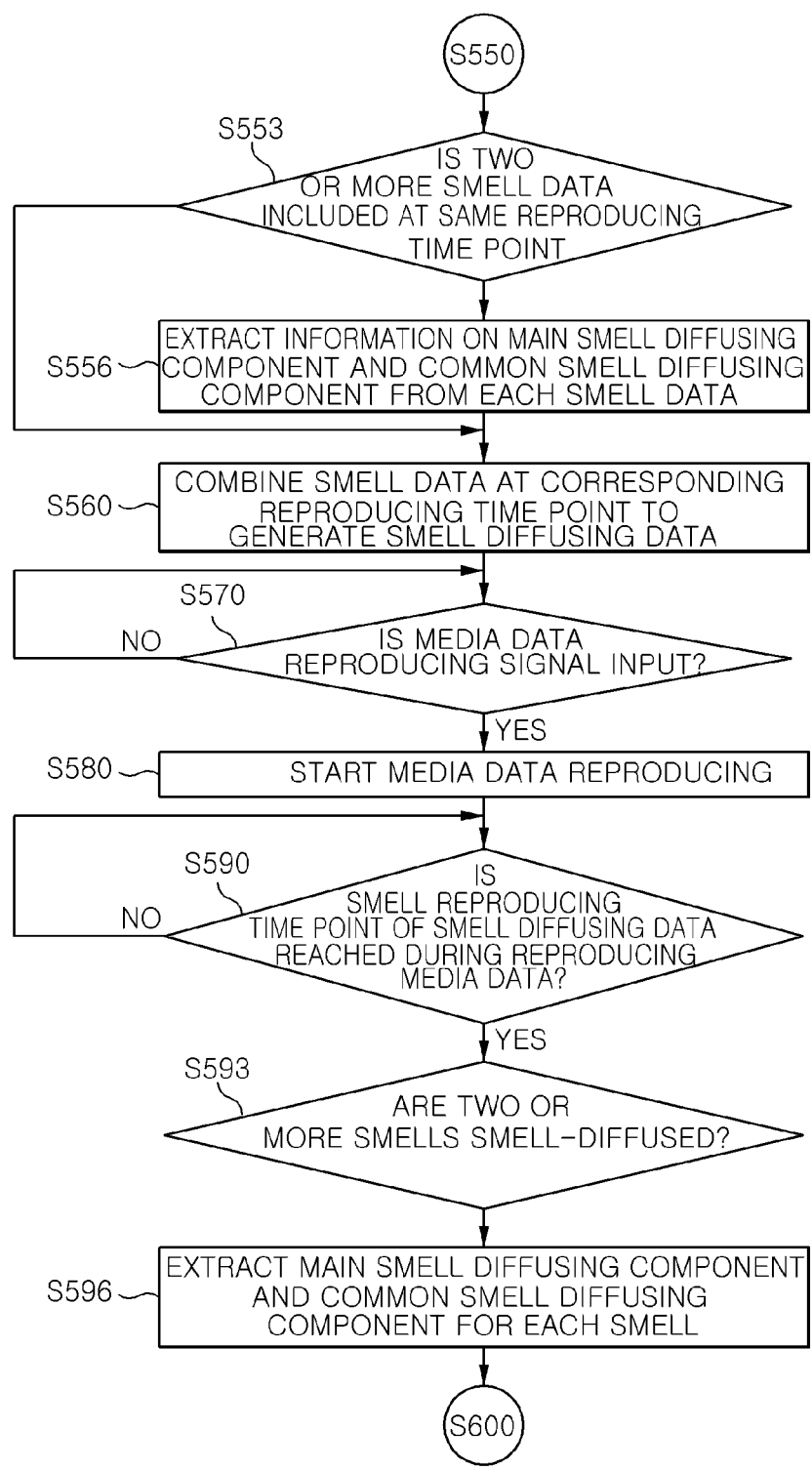

GENERATING APPARATUS, REPRODUCING APPARATUS AND REPRODUCING METHOD OF CONTENTS WITH SMELL REPRODUCING INFORMATION

RELATED APPLICATIONS

The present application claims priority to Korean Patent Application Serial Number 10-2008-0107754, filed on Oct. 31, 2008, the entirety of which is hereby incorporated by reference.

BACKGROUND OF THE INVENTION

1. Field of the Invention

The present invention relates to a generating apparatus, reproducing apparatus, and reproducing method of contents with smell reproducing information, and in particular, to a generating apparatus, a reproducing apparatus, and a reproducing method of contents with smell reproducing information, which generate contents, including smell reproducing information in media data and output smell data together with the contents when executing the corresponding contents.

2. Description of the Related Art

As the use of Internet has been expanded as a basis of real life, a variety of information is commonly distributed in a media contents form over a network. Audiovisual based media contents occupy 90% or more of the Internet contents.

Recently, research for digitally encoding the audiovisual information as well as information of the five senses of human and representing them in the media contents form has progressed around the world in order to transmit more lifelike information. In other words, research for converting tactile information, smell information, and taste information into digital information and including it in the media contents has progressed. Among the senses, smell information has been evaluated to be the most effective sensory information that can be perceived in respects to media information and commercialized, because it is considered to be the sensory information that can effect the emotion of a human.

The smell research field can be largely sorted into a smell recognition field and a smell representation field. First, the smell research field defines a smell mechanism of a human and focuses on developing an apparatus capable of performing a function similar to the smell organ of a human. On the other hand, the smell representation field standardizes the smell information, reproduces it by using the standardized smell information, and focuses on the development of service using the smell information.

In the smell recognition field, the most remarkable research achievement includes the smell mechanism definition of a human defined by Excel and Buck, 2004. In addition to the biological accessing method, a research method in view of a technical aspect may include an electronic nose. An electronic nose has been developed since 1980 by imitating a smell organ of a human. Recently, the technical development of the electronic nose capable of accurately determining various smells has been exerted.

In the smell representation field, a method capable of reproducing smells according to smell information has been developed. The smell reproducing service using the Internet such as ScentDome by Trinsenx Co., USA and IPSmell by AromaJet Co., USA in addition to a smelling TV by ScentTV, USA has been provided since 2000, which started from a service that provides smells when showing a movie from 1960. In addition to this, Tokyo Institute of Technology in Japan published a research result of improving concentration and actual sensation of a game by applying the smell information to the game.

As such, various services using the smell information have been developed, but the level of the smell reproducing technology remains at an infant stage and thus, is limited to reproducing only one kind of smell, not complex smells. A need exists for a development of a smell information representing technology and a smell reproducing technology that can reproduce smells similar to an actual environment in order to provide the actual sensation of the media contents to the user. In addition, a need also exists for a technology development that can reproduce complex smells.

SUMMARY OF THE INVENTION

It is an object of the present invention to provide contents with a plurality of smell reproducing information by standardizing a plurality of smell information and adding smell reproducing information on a plurality of smells to existing media data based on the standardized smell information.

Further, it is another object of the present invention to provide a generating apparatus, a reproducing apparatus, and a reproducing method of contents with smell reproducing information capable of realistically reproducing media contents by effectively processing a plurality of smell information when reproducing media data.

In order to achieve the above objects, there is provided a reproducing apparatus of contents according to the present invention, including: a contents controller that detects media data, a plurality of smell data, and smell reproducing information on the plurality of smell data from contents including the smell data; a media controller that outputs reproducing instructions of the media data detected by the contents controller to a media player; and a smell diffusing controller that sorts the plurality of smell data detected by the contents controller for each reproducing period according to the smell reproducing information and controls the operation of smell diffusing apparatuses according to smell diffusing data generated by combining the corresponding smell data for each reproducing period. At this time, the smell diffusing data includes at least one of a kind of smells and smell diffusing component information and reproducing information on each smell at a corresponding reproducing time point.

The smell diffusing controller sorts into a reproducing time point where the reproducing periods overlap with each other and a reproducing time point where the reproducing periods do not overlap with each other from each smell data, when the reproducing periods for two or more smell data are overlapped with each other.

Meanwhile, the smell diffusing controller combines main smell diffusing component information from each smell data to generate the smell diffusing data and combines common smell diffusing component information from the two or more smell data to generate the smell diffusing data, when there are two or more smell data at the corresponding reproducing time point. Further, the smell diffusing controller combines the common smell diffusing component information and other main smell diffusing component information on two or more smell data to generate the smell diffusing data when there are two or more smell data at the corresponding reproducing time point.

In addition, the smell diffusing apparatus combines and discharges at least one corresponding smell diffusing component according to the smell diffusing data.

In order to achieve the above objects, there is provided a generating apparatus of contents, including: a storage unit including a contents storage unit that stores contents and a smell storage unit that stores smell data including component information and characteristic information on each of a plurality of smells and stores smell reproducing information with reproducing information on a plurality of smells corresponding to the contents; a controller including a smell information management unit that detects corresponding smell data according to the smell reproducing information when calling media data from the contents storage unit; and a contents generator that generates contents including the smell data detected by the smell information management unit, the smell reproducing information, and the called media data and stores them in the storage unit.

The smell data includes information on the main smell diffusing component and the other smell diffusing component of the corresponding smell and the smell reproducing information includes at least one of the number of smells, a kind of smell, smell reproducing concentration, a smell reproducing time point, a smell reproducing time, a smell reproducing interval, and a smell reproducing direction.

The smell information management unit provides identification codes to each of the plurality of smells and detects the corresponding smell data from the identification codes for each smell included in the smell reproducing information.

Meanwhile, the generating apparatus of contents according to the present invention further includes a user input unit that receives smell information and smell reproducing information on each of the plurality of smells and a communication unit that transmits the contents generated by the contents generator to the external reproducing apparatus of contents.

Moreover, in order to achieve the above objects, there is provided a reproducing method of contents according to the present invention, including: analyzing contents including smell data to detect media data, a plurality of smell data, and smell reproducing information on the plurality of smell data from the contents by a contents controller; sorting the plurality of smell data for each reproducing period according to the smell reproducing information and combining the corresponding smell data for each reproducing period in order to generate the smell diffusing data by a smell diffusing controller; and combining and smell-diffusing the corresponding smell diffusing component according to the smell diffusing data when the smell diffusing data is arrived at the reproducing time point while the media data is reproduced by the smell diffusing controller.

The smell reproducing information includes at least one of the number of smells, a kind of smell, smell reproducing concentration, a smell reproducing time point, a smell reproducing time, a smell reproducing interval, and a smell reproducing direction and the smell diffusing data includes at least one of a kind of smell and smell diffusing component information and reproducing information on each smell at the corresponding reproducing time point.

In addition, the generating the smell diffusing data includes sorting into a reproducing time point where the reproducing periods overlap with each other from each smell data and a reproducing time point where the reproducing periods do not overlap with each other, when reproducing periods for two or more smell data are overlapped with each other Meanwhile, the generating the smell diffusing data combines the main smell diffusing component information from each smell data to generate the smell diffusing data and combines common smell diffusing component information on the two or more smell data to generate the smell diffusing data when there are two or more smell data at the corresponding reproducing time point.

Further, the generating the smell diffusing data combines the common smell diffusing component information and other main smell diffusing component information on two or more smell data when there are two or more smells diffused at the corresponding reproducing time point to generate the smell diffusing data.

The present invention provides the identification codes to the plurality of smell information and databases them, making it possible to identify the information on each smell and the smell data for at least one smell and adds the reproducing information on the corresponding smell data to the existing media data when generating the media data, making it possible to provide the contents with the plurality of smell reproducing information.

In addition, in executing the contents with the plurality of smell reproducing information, the actual sensation of the user can be increased at the time of reproducing the media contents by linking and reproducing the smell data and the media data according to the smell reproducing information included in the contents.

Moreover, the smell diffusing apparatus includes the plurality of smell diffusing components and combines the smell diffusing components corresponding to at least two smell data and discharges them to the outside, making it possible to effectively process the information on the plurality of smells according to the reproducing of the complex smells.

BRIEF DESCRIPTION OF THE DRAWINGS

FIGS. 4 and 5 are flowcharts showing a flow of the generating operation of contents for the generating apparatus of contents with the smell reproducing information according to the present invention; and FIGS. 6 and 7 are flowcharts showing a flow of the generating operation of contents for the generating apparatus of contents with the smell reproducing information according to the present invention.

DETAILED DESCRIPTION OF THE PREFERRED EMBODIMENTS

Hereinafter, exemplary embodiments of the present invention will be described with reference to the accompanying drawings.

Figure 1:
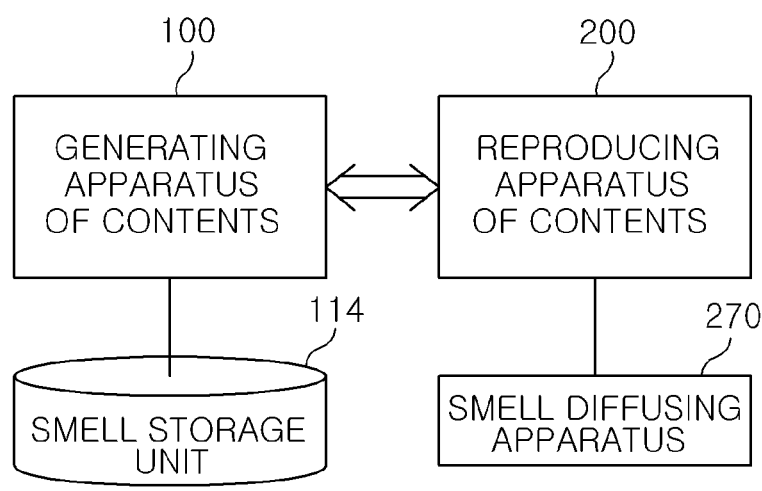
FIG. 1 is a schematic diagram showing a generating apparatus and reproducing apparatus of contents with smell reproducing information according to the present invention.

FIG. 1 is a schematic diagram showing a configuration for a generating apparatus and a reproducing apparatus of contents with smell reproducing information according to the present invention. As shown in FIG. 1, the present invention will be described by largely dividing a generating apparatus 100 of contents that generates contents with smell reproducing information and a providing apparatus 200 of contents that reproduces contents generated by the generating apparatus 100 of contents.

Herein, the generating apparatus 100 of contents receives the smell information including component information and characteristic information on each of the plurality of smells from a user, databases each smell data in a form that can identify the plurality of smell information, and stores them in a smell storage unit 114. Of course, the smell data for each of the plurality of smells may be received from the outside. Further, the generating apparatus 10 of contents generates the contents including the smell data stored in a smell storage unit 114. At this time, the generating apparatus 100 of contents detects the corresponding smell data according to the smell reproducing information, which is input from the user or received from the outside, to generate the contents, including the detected smell data and smell reproducing information to the corresponding media data. In addition, the smell reproducing information may be detected from the media data.

In FIG. 1, the smell storage unit 114 is implemented by a separate storage unit and may be connected to the generating apparatus 100 of contents by a wired or wireless communication scheme. However, the case where the smell storage unit 114 may be implemented inside the generating apparatus 100 of contents and in FIG. 2, the smell storage unit 114 may be implemented inside the generating apparatus 100 of contents, will be described by way of example.

Meanwhile, the generating apparatus 200 of contents is an apparatus that receives the contents generated from the generating apparatus 100 of contents and reproduces the corresponding contents, includes a smell diffusing device 270 to reproduce the smell data included in the contents. At this time, the reproducing apparatus 200 of contents analyzes the contents provided from the generating apparatus 100 of contents to separate the media data and the smell data and when reproducing the media data, reproduces the corresponding smell data together therewith based on the smell reproducing information. Herein, the smell diffusing apparatus 270 may be implemented inside the reproducing apparatus 200 of contents, while it is provided separately from the reproducing apparatus 200 of contents, such that it can be operated by being connected to the reproducing apparatus 200 of contents by a wired or wireless communication scheme.

In the embodiment of the present invention, the generating apparatus 100 of contents and the reproducing apparatus 200 of contents are separately implemented by way of example. However, the generating apparatus 100 of contents and the reproducing apparatus 200 of contents are implemented inside one apparatus, such that they can be operated separately.

Accordingly, the detailed description of the generating apparatus of contents and the reproducing apparatus of contents will be described with reference to the description of FIG. 2.

Figure 2:
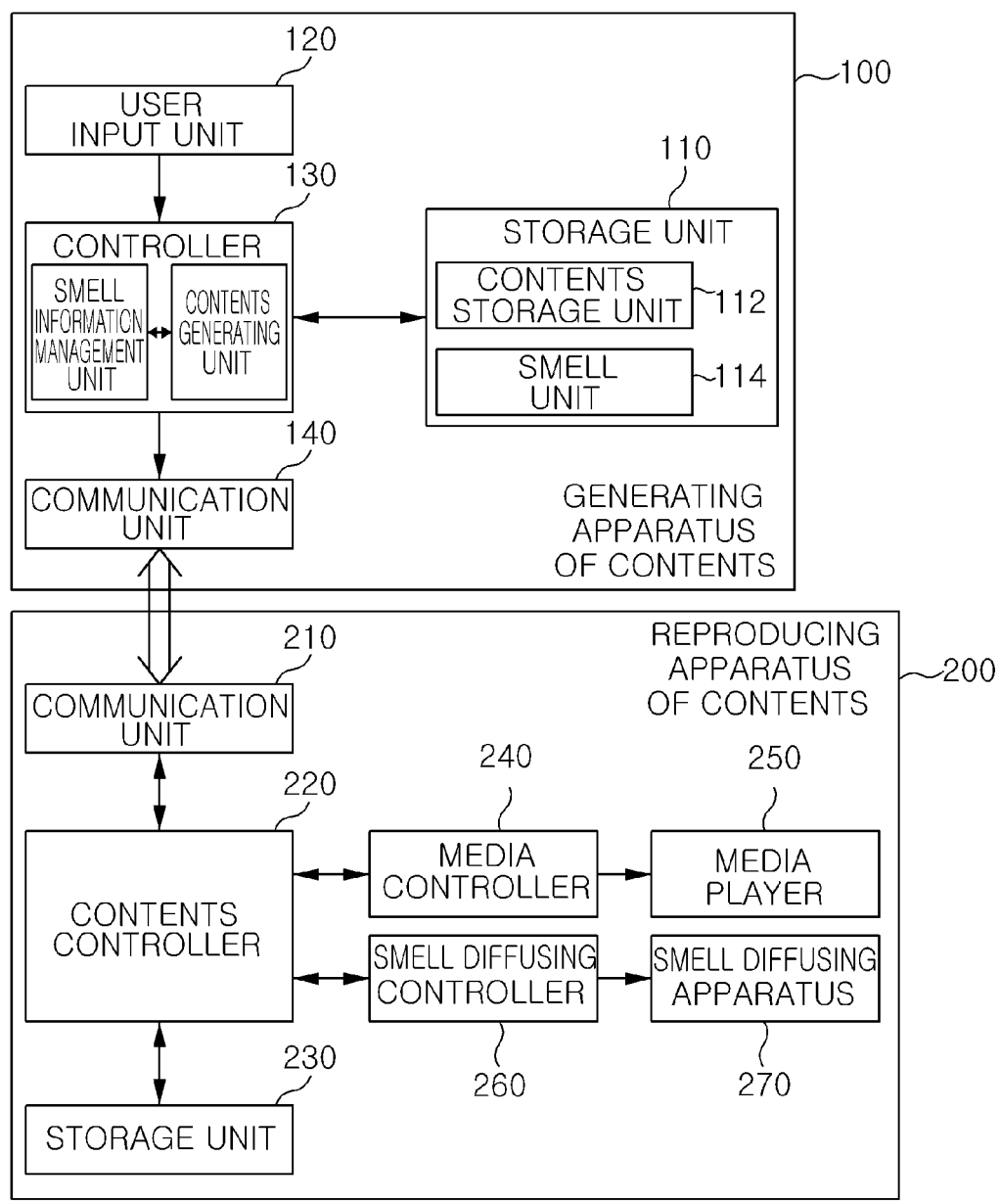
FIG. 2 is a block diagram for explaining a configuration of the generating apparatus and reproducing apparatus of contents with smell reproducing information according to the present invention.

FIG. 2 refers to a drawing for explaining a configuration of the providing apparatus of contents with the smell reproducing information according to the present invention and is a block diagram showing a configuration of the generating apparatus of contents and the reproducing apparatus of contents.

First, describing the configuration of the generating apparatus 100 of contents according to the present invention with reference to FIG. 2, the generating apparatus 100 of contents includes a storage unit 110, a user input unit 120, a controller 130, and a communication unit 140.

The storage unit 110 includes a smell storage unit 114 in which the smell data for each of the plurality of smells are stored. At this time, the smell storage unit 114 is stored with the identification codes corresponding to the plurality of smell data, the identification codes identifying each of the plurality of smell data.

For example, the smell storage unit 114 stores the smell data for each of the plurality of smells, for example, flower smell such as rose smell, chrysanthemum smell, lily smell, etc., fruit smell such as apple smell, peppermint smell, etc., hot smell such as red pepper smell, pepper smell, onion smell, etc. At this time, when the smell information of the rose smell is input, the controller 130 provides the identification code such as 'S_ROSE001' to the input rose smell, generates the smell data for the rose smell, and stores them in the smell storage unit 114. Of course, the identification code information provided to each smell data may be stored separately. Thereafter, when inputting the smell reproducing information on the media data, the corresponding smell data is extracted from the identification code included in the smell reproducing information.

Further, the storage unit 110 further includes the contents storage unit 112 in which the plurality of contents are stored. The contents storage unit 112 stores the contents such as the media data and the contents generated by including the smell data in the media data.

The user input unit 120 is a unit receiving predetermined control instructions by the external user and the user inputs the smell information on each of the plurality of smells through the user input unit 120. At this time, the smell information includes the component information and characteristic information on each smell. At this time, the controller 130 provides the identification codes to the plurality of smell information input through the user input unit 120 to generate the smell data and stores the generated smell data in the smell storage unit 114.

Further, the user input unit 120 receives the smell reproducing information on the specific media data. In other words, the user calls any one media data and at this time, inputs the smell reproducing information on the corresponding media data. Herein, the smell reproducing information includes at least one of the number of smells to be reproduced together with the called media data, a kind of smell, reproducing concentration, a reproducing time point, a reproducing time, a reproducing interval, and a reproducing direction. Of course, the smell reproducing information may be one received through the communication unit 140.

The controller 130 includes a smell information management unit 132 that manages the smell data stored in the smell storage unit 114 and a contents generator 134 that generates the contents including the media data and the smell data and stores them in the contents storage unit.

The smell information management unit 132 analyzes the input smell reproducing information to detect at least one corresponding smell information when the smell reproducing information is input through the user input unit 120. At this time, the smell information management unit 132 detects the identification code corresponding to the detected smell information to detect the corresponding smell data among the smell data stored in the smell storage unit 114 and to provide them to the contents generator 134. Therefore, the contents generator 134 generates the smell reproducing information and the contents including the detected smell data and media data. At this time, the generated contents are stored in the contents storage unit 112.

The communication unit 140 includes a module that supports the communication interface in the wired or wireless scheme. Herein, the communication unit 140 transmits the contents including the smell data stored in the contents storage unit 112 to the external reproducing apparatus 200 of contents or the external storing apparatus of contents (not shown) according to the request of the controller 130.

Meanwhile, describing a configuration of the reproducing apparatus 200 of contents according to the present invention, the reproducing apparatus 200 of contents includes a communication unit 210, a contents controller 220, a storage unit 230, a media controller 240, a media player 250, a smell diffusing controller 260, and a smell diffusing apparatus 270.

The communication unit 210 includes a module that supports the communication interface in the wired or wireless scheme. Herein, the communication unit 210 receives the contents from the external generating apparatus 100 of contents or the external storing apparatus of contents (not shown). If the smell diffusing apparatus 270 is provided separately from the reproducing apparatus 200 of contents, the smell diffusing apparatus 270 may be connected to the reproducing apparatus 200 of contents through the communication unit 210.

The contents controller 220 stores the received contents in the storage unit 230 when the contents are received by the communication unit 210. At this time, the received contents include the media data, the smell data, and the smell reproducing information on the smell data. The contents controller 220 analyzes the contents to separate the media data and the smell data and stores the separated data in the storage unit 230. Further, the contents controller 220 detects the smell reproducing information on the detected smell data and stores it in the storage unit.

In other words, the smell diffusing controller 260 detects the reproducing period of each smell data from the smell reproducing information and sorts each smell data for each reproducing period. If two or more smell data has the same reproducing period, the smell diffusing controller 260 sorts the reproducing period of each smell data into the period that corresponds to the same reproducing period and the period that does not correspond to the same reproducing period.

For example, when there are smell data A, B, and C, the smell diffusing controller 260 sorts the smell data A, B, and C for each reproducing period. At this time, when some reproducing period of the smell data B and C are overlapped with each other, the smell diffusing controller 260 sorts the smell data B into a smell data Ba corresponding to a period where the smell data B and C overlap with each other and a smell data Bb corresponding to the remaining period. Further, the smell diffusing controller 260 sorts the smell data C into a smell data Ca corresponding to a period where the smell data B and C overlap with each other and a smell data Cb corresponding to the remaining period. Therefore, the smell data A, B, and C are sorted into A, Bb, [Ba, Ca], and Ca for each reproducing period. The detailed embodiment thereof will be described with reference to FIGS. 3A and 3B.

Moreover, the smell diffusing controller 260 combines the smell data corresponding to each reproducing time point to generate the smell diffusing data. If there are two or more smell data at the corresponding reproducing period, the smell diffusing controller 260 combines the main smell diffusing component information on the corresponding smell from each smell data to generate the smell diffusing data. At this time, the smell diffusing controller 260 extracts only the common smell diffusing component information to generate the smell diffusing data when there are the common smell diffusing components among the main smell diffusing components. Herein, the smell diffusing data includes at least one of the kinds of each smell, the smell diffusing components information for each smell, and the reproducing information. At this time, the reproducing information includes the information of a smell reproducing time point, a reproducing time, reproducing concentration, a smell diffusing interval, a smell diffusing direction, etc.

Meanwhile, the contents controller 220 issues the control signal for reproducing the media data separated from the contents to the media controller 240. At this time, the media controller 240 controls the operation of the media player 250 according to the control signal applied from the contents controller 220 to reproduce the media data.

The media player 250 reproduces the corresponding media data according to the issued control signal from the media controller 240. At this time, the media player 250 may be implemented inside the reproducing apparatus 200 of contents or implemented by a separate apparatus from the reproducing apparatus 200 of contents. Although the embodiment of the present invention described one example that the media player 250 is connected according to the description of the media data as one example, it can be variously applied according to the kind of data included in the contents.

Meanwhile, the smell diffusing controller 260 confirms whether the smell diffusing data arrives at the smell diffusing reproducing time point while the media data is reproduced by the media player 250. If the corresponding smell diffusing data arrives at the smell diffusing reproducing time point, the smell diffusing controller 260 outputs the corresponding smell data and the control instruction to the smell diffusing apparatus 270 to drive the smell diffusing apparatus 270, such that the smell diffusing data are reproduced by the corresponding smell diffusing apparatus 270. Herein, the smell diffusing data can be previously transmitted to the smell diffusing apparatus 270 and the smell diffusing apparatus 270 can reproduce the corresponding smell diffusing data when applying the control instruction later from the smell diffusing controller 260.

The smell diffusing apparatus 270 holds the plurality of smell diffusing components. At this time, the smell diffusing apparatus 270 is driven according to the control instruction of the smell controller 260 and combines the corresponding smell diffusing components according to the smell diffusing information and reproducing information included in the smell diffusing data and discharges them to the outside.

If there are two or more smells that are smell-diffused from the smell diffusing data at the corresponding reproducing period, the smell diffusing apparatus 270 extracts each of the main smell diffusing components for each smell or the common smell diffusing components, which are included in the smell diffusing data, to discharge the combined smell diffusing components to the outside. At this time, the smell diffusing apparatus 270 discharges the combined smell diffusing components based on the information such as the smell diffusing interval, the smell diffusing direction, etc., which are included in the smell diffusing data.

The smell diffusing apparatus 270 may include the plurality of smell discharging units (not shown) and when the smell diffusing interval and the smell diffusing direction of the complex smells are different from each other, they each can be discharged through the plurality of smell discharging units.

Therefore, the reproducing apparatus 200 of contents according to the present invention extracts and discharges the main smell diffusing components and the common smell diffusing components that correspond to the requested smells, such that it can reproduce the plurality of smells at one time, thereby making it possible to increase the actual sensation of the user when reproducing the contents.

Figure 3:
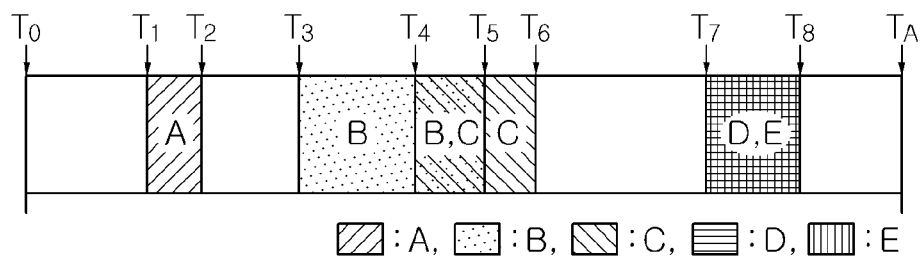
FIGS. 3A and 3B are exemplary diagrams for explaining the embodiment according to a contents reproducing operation of the reproducing apparatus of contents with the smell reproducing information according to the present invention.

FIGS. 3A and 3B show exemplary diagrams for explaining the operation of the reproducing apparatus of contents according to one embodiment and FIG. 3A shows the reproducing time of each smell data corresponding to the reproducing time of the media data and FIG. 3B shows the smell reproducing information on each smell data.

Referring to FIGS. 3A and 3B, when the contents controller 220 receives the contents from the generating apparatus 100 of contents, it separates the media data and the smell data. At this time, it can be confirmed from (a) that the reproducing time of the media data is T0~TA.

When the smell data to be reproduced together with the media data are A, B, C, D, and E, the reproducing information on each smell data A, B, C, D, and E can be confirmed from (b).

Herein, the smell data includes at least one of the kinds of each smell, the main smell diffusing components for the corresponding smells, the smell diffusing component information, and the holding time for the corresponding smell and includes the identification codes that can recognize each smell. Further, the smell reproducing information includes at least one of the reproducing time point, the reproducing concentration, the smell diffusing interval, and the smell diffusing direction for each smell data. At this time, the smells corresponding to each smell data may have different main smell diffusing components or some common smell diffusing components.

As shown in FIG. 3B, the reproducing period of the smell data A is T1:T2, the smell diffusing concentration is 5, the smell diffusing interval is 3, and the smell diffusing direction is 5. Also, the reproducing period of the smell data B is T3:T5, the smell diffusing concentration is 5, the smell diffusing interval is 4, and the smell diffusing direction is 0. Moreover, the reproducing period of the smell data C is T4:T6, the smell diffusing concentration is 7, the smell diffusing interval is 4, and the smell diffusing direction is 0. Further, the reproducing period of the smell data D and the smell data E is T7:T8, the smell diffusing concentration is 4, the smell diffusing interval is 2, and the smell diffusing direction is 3.

The smell diffusing controller 260 confirms the reproducing period of each smell data A, B, C, D, and E and sorts them into A (T1:T2), BC (T3:T6), and DE (T7:T8) and at this time, B and C and D and E having the same reproducing period into a period where the reproducing periods overlap with each other and a period where the reproducing periods do not overlap with each other are sorted. Herein, it is confirmed that the smell data D and E have the same smell reproducing information. Meanwhile, since the smell data B and C overlap with each other only a part of the reproducing period, T3:T6 is sorted into a period T3:T4 that reproduces only the smell data B, a period T5:T6 that reproduces only the smell data C, and a period T4:T5 that simultaneously reproduces the smell data B and C.

Therefore, the smell data sorted by the smell diffusing controller 260 are sorted into A, B, BC, C, and DE, respectively, according to the reproducing period. At this time, the smell diffusing controller 260 combines the smell data A, B, BC, C, and DE sorted for each reproducing interval to generate the smell diffusing data.

For example, the main smell diffusing components corresponding to the smell data A are a, f, and g, the main smell diffusing components corresponding to the smell data B are b, h, and I, and the main smell diffusing components corresponding to the smell data C are c, h, and i. Moreover, assume that the main smell diffusing components corresponding to the smell data D are d, k, and m and the main smell diffusing components corresponding to the smell data E are e, o, and p.

At this time, the smell diffusing controller 260 generates, from the smell data A, the smell diffusing data, including the information on a, f, and g, which are the main smell diffusing components, and the smell reproducing information on the smell data A. Also, the smell diffusing controller 260 generates from the smell data B, the smell diffusing data, including the information on b, h, and i, which are the main smell diffusing components, and the smell reproducing information on a period where the reproducing periods of the smell data B do not overlap with each other. Also, the smell diffusing controller 260 generates, from the smell data C, the smell diffusing data, including the information on c, h, and i, which are the main smell diffusing components, and the smell reproducing information on a period where the reproducing periods of the smell data C do not overlap with each other.

Meanwhile, the smell diffusing controller 260 generates the smell diffusing data, including the information on the main smell diffusing components b, h, and i of the smell data B, the common smell diffusing components h and I of the main smell diffusing components c, h, and j and the reproducing information on the same reproducing period of the smell data B and C. At this time, since the smell diffusing concentration of the smell data C and the smell data C are different from each other, the information of C, which is the smell diffusing data C having thick concentration, may be included in the smell diffusing data. In addition, the smell diffusing controller 260 generates the smell diffusing data, including the information on the main smell diffusing components d, k, and m of the smell data D and the main smell diffusing components e, o, and p of the smell data E and the reproducing information on the smell data D and E.

Herein, the smell diffusing controller 260 extracts only some of the main smell diffusing components according to the component ratio of the main smell diffusing components, making it possible to generate the smell diffusing data. In addition, even when there are no common smell diffusing components such as the smell data D and the smell diffusing data E, only the main smell diffusing component information having the component ratio is extracted, making it possible to generate the smell diffusing data.

Meanwhile, the smell diffusing controller 260 transmits the smell diffusing data to the smell diffusing apparatus 270 at the reproducing period corresponding to the smell data A when the reproducing time of the media data arrives at T1 time through the media player 250. Therefore, the smell diffusing apparatus 270 extracts and combines the smell diffusing components of the smell data A by the concentration of 5 from the corresponding smell diffusing data and discharges the extracted smell diffusing components at an interval of 3 in a direction of 5 until the arrival at T2 time. At this time, the smell diffusing controller 260 can separately transmit the control instruction to terminate the smell diffusing for the smell data A to the smell diffusing apparatus 270 when the reproducing time of the media data arrives at T2 time. Meanwhile, the smell diffusing apparatus 270 can automatically terminate the smell diffusing by the smell diffusing data.

In addition, the smell diffusing controller 260 transmits the smell diffusing data to the smell diffusing apparatus at the reproducing period corresponding to the smell diffusing data B when the reproducing time of the media data arrives at T3 time 270 through the media player 250. Therefore, the smell diffusing apparatus 270 extracts and combines the smell diffusing components of the smell data B by the concentration of 5 from the corresponding smell diffusing data and discharges the extracted smell diffusing components at an interval of 4 until the arrival at T4 time. Similarly, the smell diffusing controller 260 can separately transmit the control instruction to terminate smell diffusing for the smell data B to the smell diffusing apparatus 270 when the reproducing time of the media data arrives at T4 time.

Further, the smell diffusing controller 260 transmits the smell diffusing data corresponding to the smell diffusing data BC to the smell diffusing apparatus 270 through the media player 250 when the reproducing time of the media data arrives at T4 time. At this time, the smell diffusing apparatus 270 extracts the common smell diffusing components by the concentration of 5 from the corresponding smell diffusing data and extracts and combines the main smell diffusing component c of the smell data by the concentration of 2. Such combined smell diffusing components discharge at an interval of 4 in a front direction until the reproducing time of the media data arrives at T5 time.

Moreover, the smell diffusing controller 260 transmits the smell diffusing data corresponding to the smell data C to the smell diffusing apparatus 270 through the media player 250 when the reproducing time of the media data arrives at T5 time. Therefore, the smell diffusing apparatus 270 extracts and combines the main smell diffusing components of the smell data C by the concentration of 7 from the corresponding smell diffusing data and discharges the extracted smell diffusing components at an interval of 4 in a front direction until the reproducing time of the media data arrives at T6 time. Similarly, the smell diffusing controller 260 can separately transmit the control instruction to terminate smell diffusing for the smell data C to the smell diffusing apparatus 270 when the reproducing time of the media data arrives at T6 time.

Meanwhile, the smell diffusing controller 260 transmits the smell data corresponding to the smell diffusing data DE to the smell diffusing apparatus 270 through the media player 250 when the reproducing time of the media data arrives at T7 time. Therefore, the smell diffusing apparatus 270 extracts and combines the common smell diffusing components by the concentration of 4 from the corresponding smell diffusing data. The smell diffusing component of such an extracted smell diffusing data D and E is discharged at an interval of 2 in a direction of 3 until the reproducing time of the media data arrives at T8 time.

The operation of the present invention configured as described above will now be described.

Figure 4:
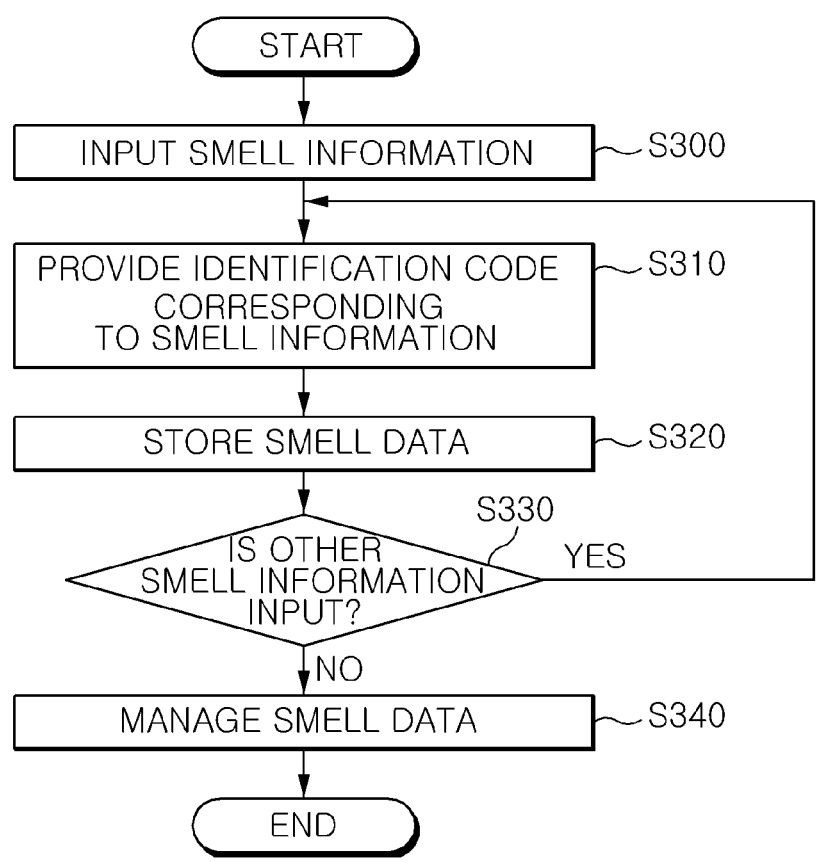

FIGS. 4 and 5 are flowcharts illustrating an operation flow of the generating apparatus of contents according to one embodiment of the present invention.

First, FIG. 4 shows a process of generating the smell data from the generating apparatus 100 of contents according to one embodiment of the present invention.

Referring to FIG. 4, the generating apparatus 100 of contents receives the smell information through the user input unit 120. At this time, the input smell information includes the kind of smell, the characteristic information on the smells, the smell diffusing component information on the corresponding smell, etc.

The contents generator 130 provides the identification code to the input smell information and generates the smell data including the smell information and the identification code provided to the corresponding smell information and stores them in the storage unit 110. At this time, the contents generator 130 can separately store the identification information corresponding to each smell data.

Meanwhile, when other smell information is input from the user, the contents generator 130 repetitively executes 'S300' to 'S320' processes, thereby generating the plurality of smell data. The contents generator 130 manages the plurality of generated smell data based on the identification codes corresponding to each smell data.

FIG. 5 shows a process of generating the contents including the smell reproducing information from the generating apparatus of contents according to one embodiment of the present invention. Referring to FIG. 5, the contents generator 130 detects the media data according to the request of the user. Herein, the media data may be the media data stored in the storage unit 110 of the generating apparatus 100 of contents and may be the media data received from the outside.

When the smell reproducing information is input through the user input unit 120, the generating unit 130 of contents detects the smell data corresponding to the input smell reproducing information. At this time, the contents generator 130 confirms the identification codes of the corresponding smells from the smell reproducing information and detects the smell data corresponding to the identification codes. Therefore, the contents generator 130 synchronizes the media data and the smell data based on the smell reproducing information and at this time, generates the contents including the media data, the smell data, and the smell reproducing information. The generated contents are stored in the contents storage unit 112.

Meanwhile, the contents generator 130 transmits the contents generated in the 'S440' process to the external reproducing apparatus 200 of contents or the external storing apparatus of contents. Of course, when the generating apparatus 100 of contents and the reproducing apparatus 200 of contents are implemented in one apparatus, the 'S450' process can be omitted.

FIGS. 6 and 7 are flowcharts illustrating an operation flow of the generating apparatus of contents according to one embodiment of the present invention.

Referring first to FIG. 6, when the reproducing apparatus 200 of contents receives the contents from the external or internal generating apparatus 100 of contents (S500), the contents controller 220 reads the received contents (S510) to confirm whether the corresponding contents includes the smell data (S520). If the received contents do not include the smell data, the contents controller 220 transmits the media data included in the contents to the media controller 240 and the media controller 240 executes the general media data reproducing operation for the corresponding media data (S640).

Meanwhile, when the received contents include the smell data, the contents controller 220 separates the media data and the smell data from the contents (S530). Further, the contents controller 220 detects the smell reproducing information on the smell data from the contents. At this time, the contents controller 220 transmits the media data to the media controller 240 and the smell data and the smell reproducing information on the smell data to the smell diffusing controller 260. The smell diffusing controller 260 confirms the reproducing information on the smell data from the smell reproducing information transmitted from the contents controller 220 (S540) and sorts the smell data for each reproducing period (S550). Moreover, the smell diffusing controller 260 combines the smell diffusing data corresponding to each reproducing period to generate the smell diffusing data (S560).

When the media controller 240 receives the reproducing signal for the media data transmitted from the contents controller 220 (S570), it controls the operation of the media player 250 to reproduce the corresponding media data (S580). The smell diffusing controller 260 confirms whether the smell diffusing data arrives at the smell diffusing reproducing time point during the reproducing of the media data when the media data starts to reproduce by the media player 250 (S590). If the smell diffusing data arrives at the reproducing time point, the smell diffusing controller 260 transmits the smell diffusing data at the corresponding reproducing period to the smell diffusing apparatus 270, such that the smell diffusing data is smell-diffused through the corresponding smell-diffusing apparatus 270. At this time, the smell diffusing apparatus 270 extracts and combines at least one diffusing components according to the kinds of smells and the smell diffusing component information and the reproducing information on each smell, which are included in the smell diffusing data, and discharges the combined smell diffusing component to the outside.

Meanwhile, the smell diffusing controller 260 repetitively executes 'S590' and 'S600' processes when the smell diffusing data are to be reproduced during the reproducing of the media data (S610), such that the media data and the smell diffusing data are linked to each other to be reproduced.

When the reproducing of the media data completes or the reproducing of the media data intends to forcibly terminate by the request of the user (S620), the media controller 240 transmits stop instructions to the media player 250 to stop the media player 250, thereby terminating the reproducing of the media data.

FIG. 7 is a flowchart showing the operation flow in the case where the reproducing periods for two or more smell data are overlapped with each other while the processes of FIG. 6 are executed.

After executing the 'S500' to 'S550' processes in FIG. 6, when there are two or more smell data at the same reproducing period among the smell data sorted for each reproducing period in the 'S550' process (S553), the smell diffusing controller 260 extracts the information on the common smell diffusing component from the main smell diffusing component of each smell data at the corresponding reproducing period (S556). At this time, the smell diffusing controller 260 combines the information on the main smell diffusing components extracted from each smell data to generate the smell diffusing data (S560). If there are the common smell diffusing components among the extracted main smell diffusing components, the smell diffusing controller 260 combines the information on the common smell diffusing component to generate the smell data.

Meanwhile, when the media controller 240 receives the reproducing signal for the media data transmitted from the contents controller 220 (S570), it controls the operation of the media player 250 to reproduce the corresponding media data (S580). The smell diffusing controller 260 confirms whether the smell diffusing data arrives at the smell diffusing reproducing time point during the reproducing of the media data when the media data starts to reproduce by the media player 250 (S590).

If the smell diffusing data arrives at the reproducing time point, the smell diffusing controller 260 transmits the smell diffusing data at the corresponding reproducing period to the smell diffusing apparatus 270 and the smell diffusing apparatus 270 performs the smell diffusing according to the kinds of smells and the smell diffusing component information and the reproducing information on each smell, which are included in the smell diffusing data. At this time, the smell diffusing apparatus 270 extracts and combines each of the smell diffusing components when there are the plurality of smell diffusing component information included in the smell diffusing data and discharges the combined components to the outside.

Meanwhile, the smell diffusing controller 260 executes processes after 's600' of FIG. 6 while the media data are reproduced, such that the media data and the smell diffusing data are linked with each other to be reproduced.

As described above, the generating apparatus, reproducing apparatus, and reproducing method of contents with smell reproducing information according to the present invention are not limited to the configuration and method of the embodiments described as above, but the embodiments may be configured by selectively combining all the embodiments or some of the embodiments so that various modifications can be made.

What is claimed is:

1. A reproducing apparatus comprising:
   a contents controller that detects media data, a plurality of smell data, and smell reproducing information indicating reproducing periods in which the plurality of smell data detected by the contents controller are to be reproduced from contents including the plurality of smell data;
   a media controller that outputs reproducing instructions of the media data detected by the contents controller to a media player so that the media player reproduces the media data; and
   a smell diffusing controller that
      sorts the plurality of smell data detected by the contents controller in accordance with the smell reproducing information detected by the contents controller to thereby determine time periods within respective reproduction periods of the reproducing periods in which different smell data of the plurality of smell data overlap and time periods within respective reproduction periods of the reproducing periods in which different smell data of the plurality of smell data do not overlap, and
      controls an operation of a smell diffusing apparatus according to smell diffusing data generated by combining the plurality of smell data detected by the contents controller with corresponding time periods of said time periods within respective reproduction periods of the reproduction periods in which different smell data of the plurality of smell data overlap and said time periods within the respective reproduction periods of the reproduction periods in which different smell data of the plurality of smell data do not overlap, so that the smell diffusing data is smell-diffused through the smell diffusing apparatus at timings which correspond to the reproduction of the media data by the media player for the smell diffusing data,
   wherein, when there are two or more smell data at a corresponding reproducing period, the smell diffusing controller combines common smell diffusing component information from the two or more smell data to generate the smell diffusing data.

2. The reproducing apparatus of contents according to claim 1, wherein the smell diffusing data includes at least one of smell diffusing component information and reproducing information on each smell at a corresponding reproducing period.

3. The reproducing apparatus of contents according to claim 1, wherein the smell diffusing controller combines the common smell diffusing component information and other main smell diffusing component information from the two or more smell data to generate the smell diffusing data.

4. The reproducing apparatus of contents according to claim 1, wherein, when there are two or more smell data at a corresponding reproducing period, the smell diffusing apparatus combines and discharges corresponding smell diffusing components of the two or more smell data according to the smell diffusing data.

* * * * *